United States Patent
Crowley et al.

(10) Patent No.: US 6,324,418 B1
(45) Date of Patent: Nov. 27, 2001

(54) PORTABLE TISSUE SPECTROSCOPY APPARATUS AND METHOD

(75) Inventors: Robert J. Crowley, Sudbury; Mark A. Hamm, Lynnfield, both of MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

(21) Appl. No.: 08/940,464

(22) Filed: Sep. 29, 1997

(51) Int. Cl.$^7$ ........................................... A61B 6/00
(52) U.S. Cl. ............................. 600/476; 600/179
(58) Field of Search ........................ 600/473, 476, 600/477, 478, 160, 178, 179; 606/14

(56) References Cited

U.S. PATENT DOCUMENTS

| | | | |
|---|---|---|---|
| 2,002,559 | 5/1935 | Waggler | 174/89 |
| 2,583,937 | 1/1952 | Fossati | 128/4 |
| 3,176,114 | 3/1965 | Kneisley | 219/223 |
| 4,233,493 | 11/1980 | Nath | 219/354 |
| 4,274,706 | 6/1981 | Tangonan | 350/96.19 |
| 4,289,966 | 9/1981 | Roberts | 250/378 |
| 4,340,307 | 7/1982 | Diamond et al. | 356/418 |
| 4,472,728 | 9/1984 | Grant et al. | 357/30 |
| 4,541,272 | 9/1985 | Bause | 73/118 |
| 4,548,505 | 10/1985 | Ono | 356/445 |
| 4,556,057 | 12/1985 | Hiruma et al. . | |
| 4,570,638 | 2/1986 | Stoddart et al. . | |

(List continued on next page.)

FOREIGN PATENT DOCUMENTS

| | | |
|---|---|---|
| 888727 | 7/1949 | (DE) . |
| 30 23 130 | 1/1982 | (DE) . |
| 40 05 743 | 8/1991 | (DE) . |
| 195 12 518 | 10/1995 | (DE) . |
| 0 314 937 | 10/1988 | (EP) . |
| 0 304 321 | 9/1992 | (EP) . |
| 0 629 380 | 12/1994 | (EP) . |
| 0 650 694 A1 | 5/1995 | (EP) . |

(List continued on next page.)

OTHER PUBLICATIONS

Meindi, J. Implantable Telemetry in Biomedical Research, Electronics Engineers' Handbook, McGraw–Hill 1989, pp 26–41—25–53.

Ko, Biomedical Sensors and Actuators, Electronics Engineers' Handbook, McGraw–Hill 1989, pp 26–53—26–68.

Coleman et al., "Acoustic Emission and Sonoluminescence Due to Cavitation at the Beam Focus of an Electrohydraulic Shock Wave Lithotripter", *Ultrasound in Med. Biol,* vol. 18, No. 3, pp. 267–281 (1992).

Vona et al., "A Test of the Hypothesis that Cavitation at the Focal Area of an Extracorporeal Shock Wave Lithotripter Produces Far Ultraviolet and Soft X–Ray Emissions", *J. Acoust, Soc. Am.,* vol. 98 (2), pp. 706–711, (Aug. 1995).

Cothren et al., "Gastrointestinal Tissue Diagnosis by Laser–Induced Fluorescence Spectroscopy at Endoscopy" *Gastro Endoscopy,* vol. 36 No. 2, pp. 105–111, 1990.

(List continued on next page.)

*Primary Examiner*—Marvin M. Lateef
*Assistant Examiner*—Shawna J Shaw
(74) *Attorney, Agent, or Firm*—Testa, Hurwitz & Thibeault, LLP

(57) ABSTRACT

A portable tissue spectroscopy apparatus includes at least one light source, at least one light detector, a power source and a controller module all disposed inside a housing that is insertable inside a body. The housing may be in the form of a hand-holdable probe or in the form of a capsule that can be swallowed or implanted in the body. The probe further includes a display mounted at a proximal end of the housing for displaying tissue characteristics. The capsule further includes a transmitter mounted inside the capsule and a receiver placed outside the body for transmitting signals representative of tissue characteristics to a remote receiver.

55 Claims, 5 Drawing Sheets

U.S. PATENT DOCUMENTS

| | | |
|---|---|---|
| 4,578,061 | 3/1986 | Lemelson . |
| 4,672,972 | 6/1987 | Berke .................................... 128/653 |
| 4,718,417 | 1/1988 | Kittrell et al. .................... 128/303.1 |
| 4,768,513 * | 9/1988 | Suzuki . |
| 4,803,992 | 2/1989 | Lemelson . |
| 4,872,458 | 10/1989 | Kanshira et al. .................... 128/401 |
| 4,882,623 | 11/1989 | Uchikubo .............................. 358/98 |
| 4,894,547 | 1/1990 | Leffell et al. . |
| 4,902,896 | 2/1990 | Fertig, Sr. et al. .................. 298/348 |
| 4,928,172 | 5/1990 | Uehara et al. ........................ 358/98 |
| 4,930,516 | 6/1990 | Alfano et al. . |
| 4,938,602 | 7/1990 | May et al. ............................ 356/435 |
| 4,981,138 | 1/1991 | Deckelbaum et al. ............... 128/665 |
| 5,001,556 | 3/1991 | Nakamura et al. .................... 358/98 |
| 5,009,655 | 4/1991 | Daignault, Jr. et al. ................. 606/7 |
| 5,021,888 | 6/1991 | Kondou et al. ................. 358/213.11 |
| 5,034,010 | 7/1991 | Kittrell et al. . |
| 5,036,853 | 8/1991 | Jeffcoat et al. . |
| 5,042,494 | 8/1991 | Alfano ................................. 128/665 |
| 5,045,056 | 9/1991 | Behl ....................................... 604/49 |
| 5,056,503 | 10/1991 | Nagasaki et al. ......................... 128/6 |
| 5,062,428 | 11/1991 | Chance . |
| 5,106,387 | 4/1992 | Kittrell et al. ........................ 606/15 |
| 5,115,137 | 5/1992 | Andersson-Engels et al. . |
| 5,116,759 | 5/1992 | Klainer et al. ....................... 435/288 |
| 5,125,404 | 6/1992 | Kittrell et al. . |
| 5,127,407 | 7/1992 | Tan ....................................... 128/633 |
| 5,131,398 | 7/1992 | Alfano et al. ........................ 128/665 |
| 5,166,755 | 11/1992 | Gat ....................................... 356/419 |
| 5,172,693 | 12/1992 | Doody . |
| 5,174,297 | 12/1992 | Daikuzono . |
| 5,187,572 | 2/1993 | Nakamura et al. .................... 358/98 |
| 5,187,672 | 2/1992 | Chance et al. . |
| 5,193,542 | 3/1993 | Missanelli et al. . |
| 5,197,470 | 3/1993 | Helfer et al. . |
| 5,201,318 | 4/1993 | Rava et al. . |
| 5,206,174 | 4/1993 | Gehrke et al. ........................ 436/58 |
| 5,213,569 | 5/1993 | Davis .................................... 604/22 |
| 5,233,621 | 8/1993 | Lawandy ............................... 372/22 |
| 5,242,437 | 9/1993 | Everett et al. ........................ 606/15 |
| 5,261,410 | 11/1993 | Alfano et al. . |
| 5,262,645 | 11/1993 | Lambert et al. ..................... 250/339 |
| 5,304,173 | 4/1994 | Kittrell et al. ........................ 606/15 |
| 5,305,748 | 4/1994 | Wilk . |
| 5,309,907 | 5/1994 | Fang et al. ........................... 128/633 |
| 5,318,024 | 6/1994 | Kittrell et al. ....................... 128/634 |
| 5,348,018 | 9/1994 | Alfano et al. . |
| 5,350,375 | 9/1994 | Deckelbaum et al. ................... 606/7 |
| 5,351,532 | 10/1994 | Hager ...................................... 73/153 |
| 5,377,676 | 1/1995 | Vari et al. ............................. 128/634 |
| 5,383,467 | 1/1995 | Auer et al. . |
| 5,386,827 | 2/1995 | Chance et al. . |
| 5,398,844 | 3/1995 | Zaslavsky et al. ................... 221/208 |
| 5,402,778 | 4/1995 | Chance . |
| 5,402,792 | 4/1995 | Kimura ........................... 128/663.01 |
| 5,405,369 | 4/1995 | Selman et al. ........................ 607/88 |
| 5,413,108 | 5/1995 | Alfano . |
| 5,417,207 | 5/1995 | Young et al. ........................ 128/634 |
| 5,419,323 | 5/1995 | Kittrell et al. . |
| 5,421,337 | 6/1995 | Richards-Kortum et al. . |
| 5,421,339 | 6/1995 | Ramanujam et al. . |
| 5,439,000 * | 8/1995 | Gunderson et al. . |
| 5,445,608 | 8/1995 | Chen et al. ............................ 604/20 |
| 5,452,723 | 9/1995 | Wu et al. . |
| 5,456,252 | 10/1995 | Vari et al. . |
| 5,461,229 | 10/1995 | Sauter et al. ......................... 250/253 |
| 5,467,767 | 11/1995 | Alfano et al. ........................ 128/665 |
| 5,512,757 | 4/1996 | Cederstrand et al. . |
| 5,517,313 | 5/1996 | Colvin, Jr. . |
| 5,542,928 | 8/1996 | Evans et al. ......................... 604/113 |
| 5,545,897 | 8/1996 | Jack . |
| 5,553,614 | 9/1996 | Chance . |
| 5,555,885 | 9/1996 | Chance . |
| 5,556,421 | 9/1996 | Prutchi et al. ......................... 607/36 |
| 5,562,100 | 10/1996 | Kittrell et al. . |
| 5,571,152 | 11/1996 | Chen et al. ............................ 607/92 |
| 5,579,773 | 12/1996 | Vo-Dinh et al. . |
| 5,617,857 * | 4/1997 | Chader et al. . |
| 5,632,740 | 5/1997 | Koch et al. . |
| 5,647,368 * | 7/1997 | Zeng et al. . |
| 5,701,902 * | 12/1997 | Vari et al. . |
| 5,769,791 | 6/1998 | Benaron et al. . |
| 5,785,658 | 7/1998 | Benaron et al. . |
| 5,792,053 * | 8/1998 | Skladnev et al. . |
| 5,800,350 * | 9/1998 | Coppleson et al. . |
| 5,807,261 | 9/1998 | Benaron et al. . |
| 5,819,736 * | 10/1998 | Avny et al. . |
| 5,842,995 * | 12/1998 | Mahadevan-Jansen et al. . |
| 5,851,181 * | 12/1998 | Talmor . |
| 5,879,289 * | 3/1999 | Yarush et al. . |
| 5,893,364 * | 4/1999 | Haar et al. . |
| 5,902,247 * | 5/1999 | Coe et al. . |
| 5,908,294 * | 6/1999 | Schick et al. . |
| 5,941,822 * | 8/1999 | Skladnev et al. . |
| 6,096,065 * | 8/2000 | Crowley ................................ 607/88 |
| 6,119,031 * | 9/2000 | Crowley et al. ..................... 600/407 |
| 6,149,591 * | 11/2000 | Henderson et al. ................. 600/407 |
| 6,185,443 * | 2/2001 | Crowley ............................... 600/407 |
| 6,238,348 * | 5/2001 | Crowley et al. ..................... 600/476 |
| 6,240,312 * | 5/2001 | Alfano et al. ........................ 600/476 |

FOREIGN PATENT DOCUMENTS

| | | |
|---|---|---|
| 0 728 440 | 8/1996 | (EP) . |
| 0 777 119 | 6/1997 | (EP) . |
| 0 792 618 | 9/1997 | (EP) . |
| 0 792 618 A1 | 9/1997 | (EP) . |
| 0 920 831 A1 | 6/1999 | (EP) . |
| 2-223828 | 9/1990 | (JP) . |
| 7 88105 | 4/1995 | (JP) . |
| 7-88105 | 4/1995 | (JP) . |
| 7-289506 | 11/1995 | (JP) . |
| 8-83569 | 3/1996 | (JP) . |
| 9-192138 | 7/1997 | (JP) . |
| WO 90/04352 | 5/1990 | (WO) . |
| WO 90/12536 | 11/1990 | (WO) . |
| WO 91/15151 | 10/1991 | (WO) . |
| WO 92/14514 | 9/1992 | (WO) . |
| WO 92/15253 | 9/1992 | (WO) . |
| WO 94/13191 | 6/1994 | (WO) . |
| WO 95/12349 | 5/1995 | (WO) . |
| WO 96/05693 | 2/1996 | (WO) . |
| WO 96/07451 | 3/1996 | (WO) . |
| WO 96/24406 | 8/1996 | (WO) . |
| WO 96/39932 | 12/1996 | (WO) . |
| WO 97/01985 | 1/1997 | (WO) . |
| WO 98/22805 | 5/1998 | (WO) . |

OTHER PUBLICATIONS

Kapadia et al, "Laser–induced fluorescence spectroscopy of human colonic mucosa", *Gastroenterology,* vol. 29, pp. 150–157, 1990.

Lilge et al., "Light Induced Fluorescennce Spectroscopy at Endoscopy", Presented at the 10th Asisan Pacific Congress of Gastroenterology, 1996.

Huang et al., "Fluorescence Diagnosis of Gynecological Cancerous and Normal Tissues", *SPIE,* vol. 2135, pp. 42–44, 1994.

Anidjar et al., "Ultraviolet Laser–Induced Autofluorescence Distinction Between Malignant and Normal Urothelial Cells and Tissues", *Journal of Biomedical Optics,* vol. 1 No.3, pp. 335–341, 1996.

Crowley et al., "Ultrasound Guided Therapeutic Catherters: Recent Developments and Clinical Results", *The International Journal of Cardiac Imaging,* vol. 6, pp. 145–156, 1991.

International Search Report for PCT/US97/20367.

International Search Report for PCT/US97/20435.

Petrofsky, "In Vivo Measurement of Brain Blood Flow in the Cat," *IEEE Transactions on Biomedical Engineering;* vol. BME–26, No. 8: 441–445 (Aug., 1979).

Internet Publication, http://iqe.ethz.ch/~fpst/Final_Report/M4/M4PO4–1.html.

Kopp et al., "Stay Tuned: Photonic Filters Color Your World," *Photonics Spectra,* Mar. 1997, pp. 125–129.

* cited by examiner

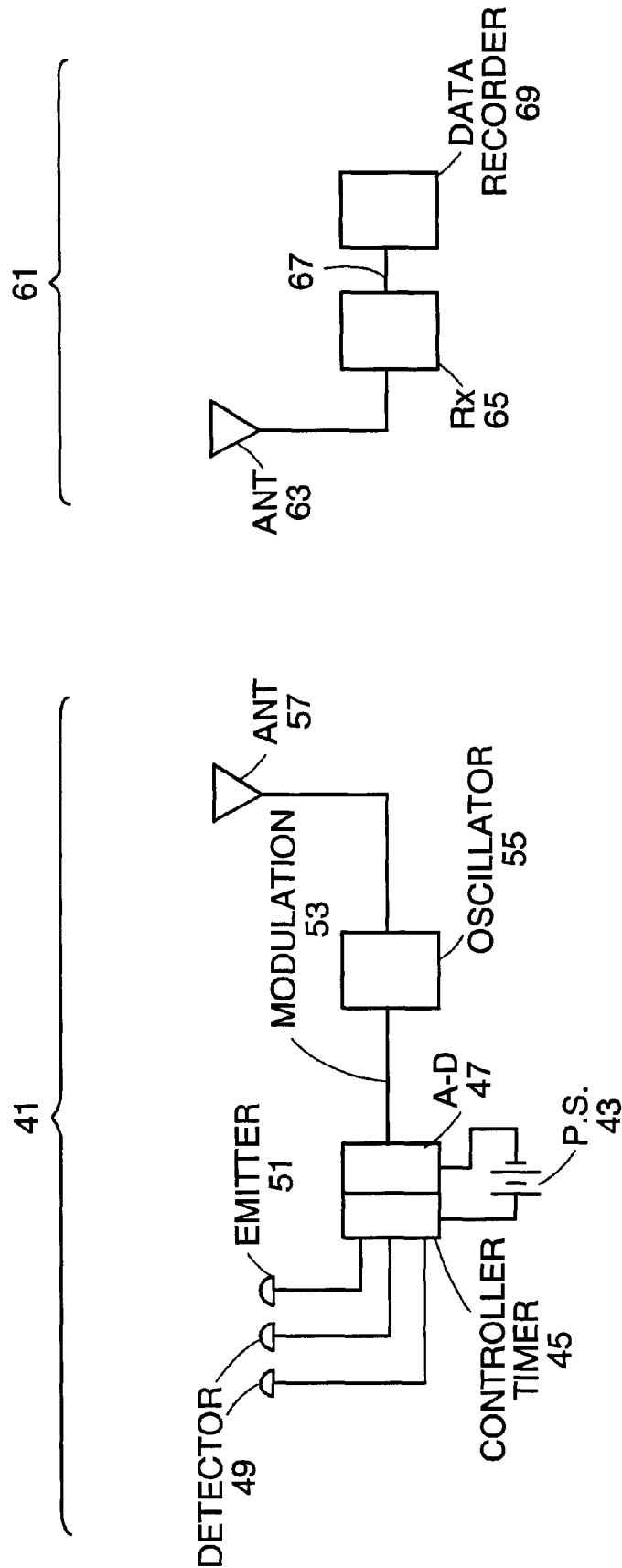

PORTABLE TISSUE SPECTROSCOPY APPARATUS AND METHOD

FIELD OF THE INVENTION

The invention relates to an apparatus and method for diagnosing tissue. More particularly, the invention relates to a portable tissue spectroscopy apparatus and a method of performing tissue spectroscopy.

BACKGROUND

Tissue spectroscopy involves determining one or more characteristics of tissue inside a body by subjecting the tissue to light and detecting spectroscopic properties of the illuminated tissue. Tissue spectroscopy techniques are undergoing rapid development. For example, numerous light sources and detectors for use in tissue spectroscopy are being tested clinically. Current tissue spectroscopy systems tend to be large, bulky and expensive as they require external power supplies, light sources and spectrometer detection equipment.

In a typical tissue spectroscopy system, the excitation light from an external light source is delivered in vivo through an optical fiber to illuminate internal tissue. The optical fiber is placed inside a probe capable of being inserted inside a body cavity. The light emitted by the illuminated tissue, which indicates tissue characteristics, is delivered to an external detector through an optical fiber also placed inside the probe. The external devices tend to be bulky because researchers are still exploring the use of various light excitation wavelengths, detection wavelengths and associated algorithms that may be found useful for detecting certain types of diseases. These diseases include cancer, displasia, various types of infections, viruses, inflammations, connective tissue disorders and autoimmune diseases.

Development of tissue spectroscopy devices tends to be slow, because research and validation work must be performed ahead of product design, which must then be approved by the various regulatory agencies, such as the U.S. Food and Drug Administration (FDA) and their foreign equivalents. To expedite the application of tissue spectroscopy, there remains a need for simple tissue spectroscopy devices that can be used in clinical settings. An example of such a device would be a portable tissue spectroscopy device which integrates all the features needed to successfully perform tissue spectroscopy in a simple housing insertable inside a body cavity. A portable tissue spectroscopy device which is simple to use and which displays the tissue spectroscopy result in an easily readable manner can also be used by patients as a self-test device.

For portable tissue spectroscopy devices to be successful, the devices need to be manufactured inexpensively and operate safely. The devices should be manufacturable with a small number of parts using existing manufacturing technologies. In addition, portable tissue spectroscopy devices should be able to protect the patients and the device operators from electrical shock and overexposure to light, which might occur with high power research units. The portable tissue spectroscopy devices should also permit reconfiguration for multiple uses over a variety of wavelengths of light, which may require the use of light wavelength ranges not typically used today, such that large amounts of hardware and expensive display equipment does not become obsolete in the future.

SUMMARY OF THE INVENTION

In one aspect, the invention relates to a tissue spectroscopy apparatus for determining characteristic of tissue in a body. In one embodiment, the apparatus includes a housing, at least one light source, at least one light detector, a power source and a display. The housing is insertable in a body cavity. The light sources illuminate tissue in the body. The light detectors detect spectroscopic properties of the illuminated tissue. The power source provides power to at least one of the light sources and at least one of the light detectors. The display may be located on a proximal end of the housing. The display indicates spectroscopic properties of the illuminated tissue.

The tissue spectroscopy apparatus can be a probe having a distal end insertable in the body cavity and a hand-holdable proximal end remaining outside the body. The distal end of the probe has a window and at least one of the light sources is positioned adjacent the window. The distal end of the housing may be angled to provide better contact between the window and the tissue. The probe can also comprise an actuator disposed adjacent a proximal end of the housing for actuating the apparatus. The probe can also include a control module disposed in the housing in communication with the power source.

In another embodiment, the invention features a tissue spectroscopy capsule for diagnosing tissue inside a body. The capsule includes a housing insertable in a body, at least one light emitter disposed in the capsule for illuminating tissue, and at least one light detector disposed in the housing for detecting spectroscopic properties of the tissue.

The capsule can include additional monitoring sensors such as pressure sensors or position sensors. The capsule can also include a transmitter disposed in the capsule and a receiver disposed external to the capsule for receiving signals from the transmitter. The receiver may be capable of storing data over a time period for subsequent recovery.

In another aspect, the invention features a method for performing tissue spectroscopy. In one embodiment, a capsule is inserted inside the body. Tissue inside the body is illuminated with at least one light source disposed in the capsule, and spectroscopic properties of the illuminated tissue is detected with at least one light detector disposed in the capsule. The capsule may further include a transmitter and a signal representative of the detected property is transmitted to a receiver outside the body. The signal is processed to provide information about the tissue.

In another embodiment, a probe is inserted in a body cavity such that a distal end of the probe is positioned adjacent tissue, while a proximal end remains outside the body cavity. The tissue is illuminated with at least one light source disposed in the probe. Spectroscopic properties of the illuminated tissue are detected with at least one light detector disposed in the probe. The detected spectroscopic properties are displayed on a display located on the proximal end of the probe.

BRIEF DESCRIPTION OF THE DRAWINGS

This invention is described with particularity in the appended claims. The above and further advantages of this invention may be better understood by referring to the following description taken in conjunction with the accompanying drawings.

FIG. 4A is a block diagram of a transmitter system disposed inside the tissue spectroscopy capsule of FIG. 2A.

FIG. 4B is a block diagram of a receiver system to be used with the transmitter system of FIG. 4A.

DETAILED DESCRIPTION

Figure 1:
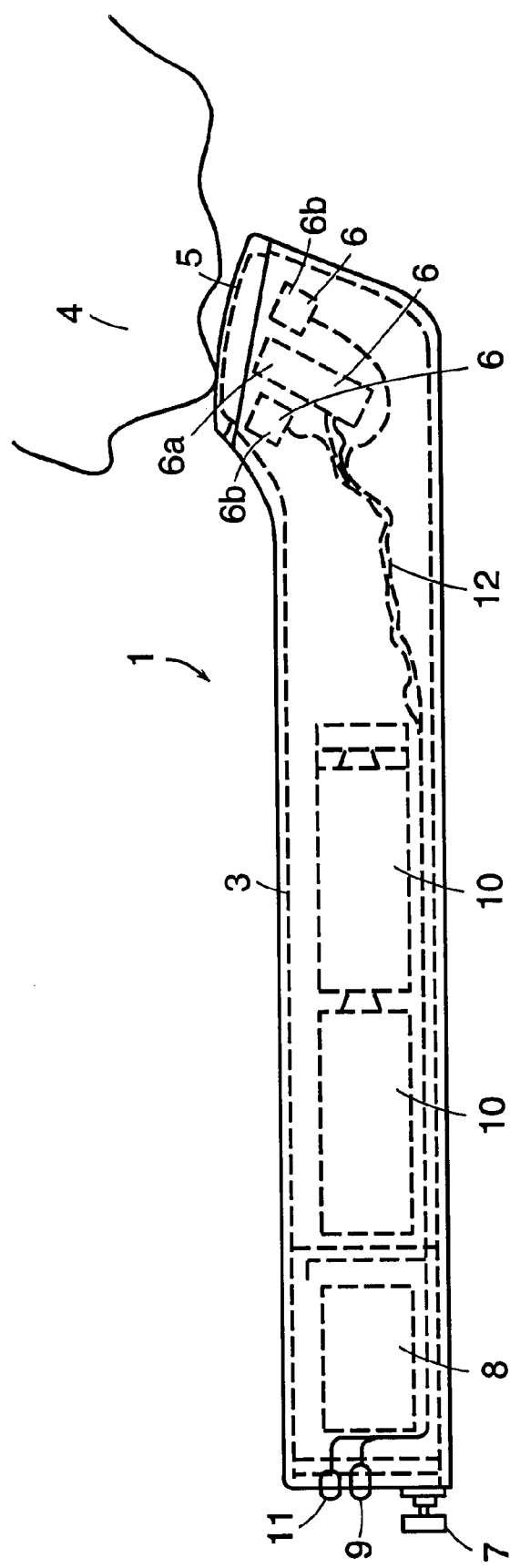
FIG. 1 is a side view of a portable tissue spectroscopy probe.

Referring to FIG. 1, a tissue spectroscopy probe 1 includes a spectroscopic component module 6, a power source 10, and a control module 8 disposed inside a housing 3. The housing includes a distal window 5, and the spectroscopic component module 6 is disposed adjacent the window 5. The probe 1 further includes a proximally mounted actuation switch 7, and indicators 9 and 11. In one embodiment, the indicator 9 is a red light, which is actuated to indicate cancerous tissue, and the indicator 11 is a green light, which is actuated to indicate normal tissue. The probe 1 is sized and shaped to fit inside a body cavity, which provides access to a tissue 4 to be examined, while the proximal end of the probe I remains outside the body for manipulation and control as well as for allowing the operator to observe the indicators 9, 11.

The probe 1 may be tapered, cylindrical or elongated in shape. The housing 3 may be constructed of a flexible material such as vinyl or polyethylene. The flexible housing 3 permits the probe 1 to be inserted inside the body cavity with greater comfort. Other materials suitable to form the housing 3 include plastics, metals or composites such as carbon fiber or glass fiber composites that exhibit low thermal conductivity. In one embodiment, the housing 3 is constructed of a material having a low thermal conductivity. Low thermal conductivity of the housing material prevents the person from feeling the coldness of the metal instruments disposed inside the housing 3 and prevents any heat that may be generated from the internal electronics from propagating out of the housing 3.

In one embodiment, the distal window 5 is constructed of glass or plastic. An example of a suitable glass is a quartz glass. In one detailed embodiment, the window 5 includes a diffuser (not shown) for scattering and diffusing the light generated by a light source 6a to provide uniform illumination of the tissue 4. In another detailed embodiment, the distal end of the probe 1 is offset or bent at an angle to provide better contact between the distal window 5 and the tissue 4 being examined. In yet another detailed embodiment, the distal end of the probe 1 is provided with an aperture (not shown), instead of a window, through which light passes to reach the tissue 4.

The spectroscopic component module 6 includes a light source 6a and light detectors 6b. Details of the spectroscopic component module 6 is described in a commonly owned, copending U.S. patent application Ser. No. 08/898,604, titled "Miniature Spectrometer" by Robert J. Crowley, which is incorporated herein by reference. The light source 6a illuminates the tissue 4, and the detectors 6b detect spectroscopic properties of the illuminated tissue 4. The light source 6a can be, for example, a laser or a diode capable of emitting light at a pre-determined wavelength. The spectroscopic component module 6 may comprise one or more light sources 6a and one or more light detectors 6b. The light source 6a and the light detectors 6b are electrically coupled to the power source 10 through cables 12.

The power source 10 is electrically coupled to the control module 8. In one embodiment, the power source 10 includes a plurality of batteries, which provide DC power to the light source 6a, the light detectors 6b, the control module 8 and the indicators 9, 11. The control module 8 performs a variety of functions including: regulating the power delivered to the light source 6a; converting the detected light from an analog to a digital signal, and providing the logical function and display driver to the indicators 9 and 11.

In performing tissue spectroscopy, the probe 1 is inserted in a body cavity such that the distal end of the probe 1 is positioned adjacent the tissue 4 while the proximal end remains outside the cavity. The tissue 4 is illuminated with light having a pre-determined wavelength generated by the light source 6a. The spectroscopic properties of the illuminated tissue 4 are detected by the light detectors 6b. The detected spectroscopic properties are converted to indicate tissue characteristics and the tissue characteristics are displayed on the indicators 9, 11.

Figure 2A:
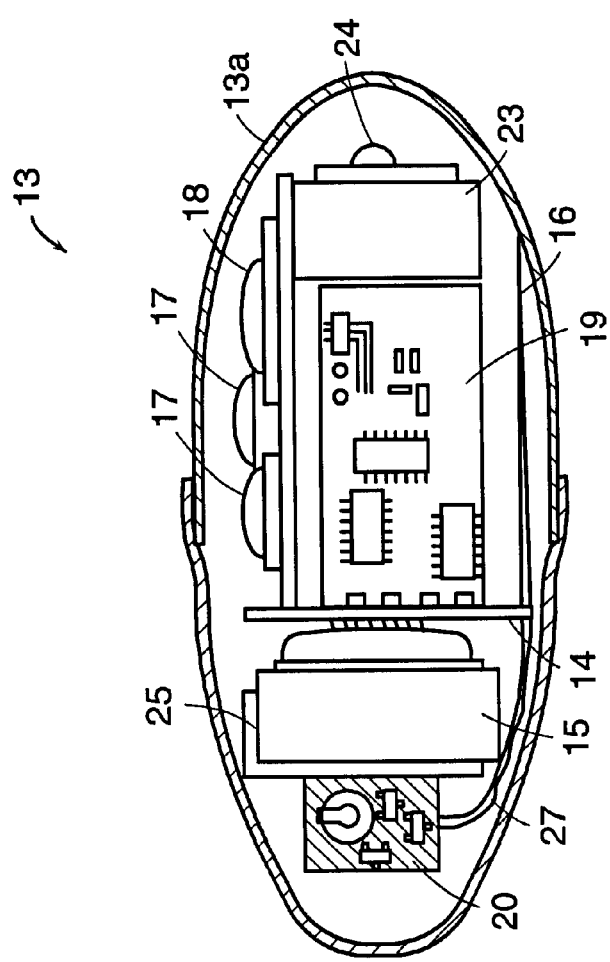
FIG. 2A is a cross-sectional view of a tissue spectroscopy capsule.

Referring to FIG. 2A, a tissue spectroscopy capsule 13 includes a housing 13a insertable in a body and at least one sensor 17 disposed in the housing 13a for obtaining spectroscopic properties of tissue in the body. The capsule 13 further includes an emitter 18, a power source 15, a controller module 19, a transmitter 20, and a transmitter antenna 16. The capsule 13 houses a self contained, fully functioning diagnostic instrument that is capable of collecting, storing and transmitting information from deep within the body, without the need for interconnecting wires, catheters, guidewires, introducers, endoscopes, guiding catheters, or sheaths. In addition, the capsule 13 may be introduced into a body without the need for incisions, and thus is useful for automated data collection from a variety of sites within the body.

The capsule housing 13a may be constructed from a biocompatible material such as a metal, plastic or a composite. The material forming the capsule housing 13a allows effective passage of light and radio frequency signals without excessive attenuation. Plastics such as polycarbonate and polyethylene and composites such as epoxy resin impregnated with glass fibers are good conductors of electromagnetic energy, and therefore, are suitable materials to form the capsule housing 13a. In one embodiment, the capsule housing 13a is flexible. In another embodiment, the capsule housing 13a is rigid.

The overall size of the capsule 13 is small enough to permit passage through a body cavity or for the capsule to be implanted in the body. A capsule 13 having a minor axis diameter of less than 1 cm and a major axis diameter of less than 2 cm easily houses conventional off-the-shelf components and fits through a human esophagus. The capsule 13 can be smaller when used with miniaturized components.

The capsule 13 houses a substrate 14 which supports the emitter 18, the sensors 17, and the controller module 19 in a compact fashion. The substrate 14 may be formed of epoxy fiberglass resin, metal, plastic or silicon, and may be equipped with conductive circuit traces (not shown). A circuit trace disposed along the inside of the capsule housing 13a performs as the transmitter antenna. In another embodiment, the capsule housing 13a itself acts as the transmitter antenna. The transmitter antenna 16 comprises a capacitive coupling element that effectively transmits radio frequency signals to an external location. In another embodiment, the transmitter 16 comprises an ultrasound transducer (not shown) that transmits acoustic signals to an external receiver.

The capsule 13 further includes a location coil 23 which provides electromagnetic position information about the capsule to outside detectors so that the progress of the capsule can be monitored. Design of such coils 23 is well known to those skilled in the art. Location coils 23, for example, have been used as catheter tip sensors. The location coils 13 may also be used for generating an image of the area within the body in which the capsule 13 is located by using magnetic resonance scanning techniques.

The capsule 13 includes one or more light emitters and one or more light detectors. The light detectors may be located in various places within the housing 13a for detecting spectroscopic properties from various tissues near the capsule 13. The capsule 13 may further include other types of emitters and sensors. The additional emitters and sensors, for example, can relate to electromagnetic radiation, pressure, temperature, x-ray radiation and/or heat. In one embodiment, the capsule 13 further comprises an acoustic transmitter and a receiver for measuring flow of fluid or for detecting echo location of the capsule 13. In another embodiment, the capsule 13 further includes diagnostic sensors such as monitoring electrodes, pressure sensors and temperature sensors.

Any of the transducers may be connected to the controller module 19 and empowered by the power source 15, which is held in place with a bracket 25. The controller module 19 inside the capsule 13 performs the following functions: timing excitation and detection; triggering light excitation; powering light detectors; performing analog to digital conversion; performing data stream conversion; modulating the transmitter carrier wave; regulating voltage and current; and other functions that are customarily provided in single and multi-integrated circuit designs.

The transmitter 20 is interconnected to the substrate 14 through wires 27. In another embodiment, the transmitter 20 is incorporated within a single integrated circuit chip (not shown) on the controller module 19. In either case, the transmitter 20 has a simple construction including a low cost oscillator, such as a surface acoustic wave or quartz crystal oscillator, for determining the frequency of the transmission and for providing sufficient energy for subsequent radiation from the transmitter antenna 16.

The capsule 13 further includes a button switch 24 which may be used to activate the capsule 13 prior to insertion inside the body by pressing the button 24. The button 24 may be pressed through a flexible wall of the capsule housing 13a.

Figure 2B:
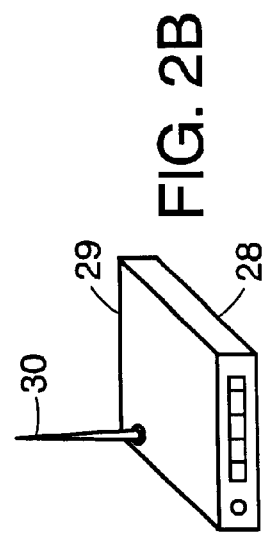
FIG. 2B is a perspective view of a receiver for use with the tissue spectroscopy capsule of FIG. 2A.

Referring to FIG. 2B, the receiver 28 receives the signals transmitted from the transmitter 20 (FIG. 2A). The receiver 28 includes a shielded housing 29 and a receiver antenna 30. The receiver 28 is located remotely from the capsule 13, i.e., outside the body. In one embodiment, the receiver 28 is placed close to the body for optimal signal transmission. In one detailed embodiment, the receiver 28 is mounted on a belt, clip or patch and placed close to the body so that the receiver 28 can detect signals as they are transmitted from the transmitter 20 regardless of the location of the body. The receiver 28 provides all of the functions of an ordinary radio receiver such as oscillation, mixing, down or up conversion, detection, amplification, filtering and demodulation.

In one embodiment, the receiver 28 houses components (not shown) which allow recording of data over time for later recovery and reading or for retransmission to another receiver/transmitter combination (not shown) such as a repeater, cellular (or the like) base station or satellite. Retransmitted data can be read and interpreted by a physician or other qualified personnel. Alternatively, data can be sent to a service that reviews the data and generates a report for a fee. The data may include a patient ID number, a billing number, a Global Positioning System (GPS) latitude and longitude derived from an on-board GPS unit placed in the recorder or the capsule 13, and an accounting system may automatically record this information to generate subsequent billing.

Figure 3:
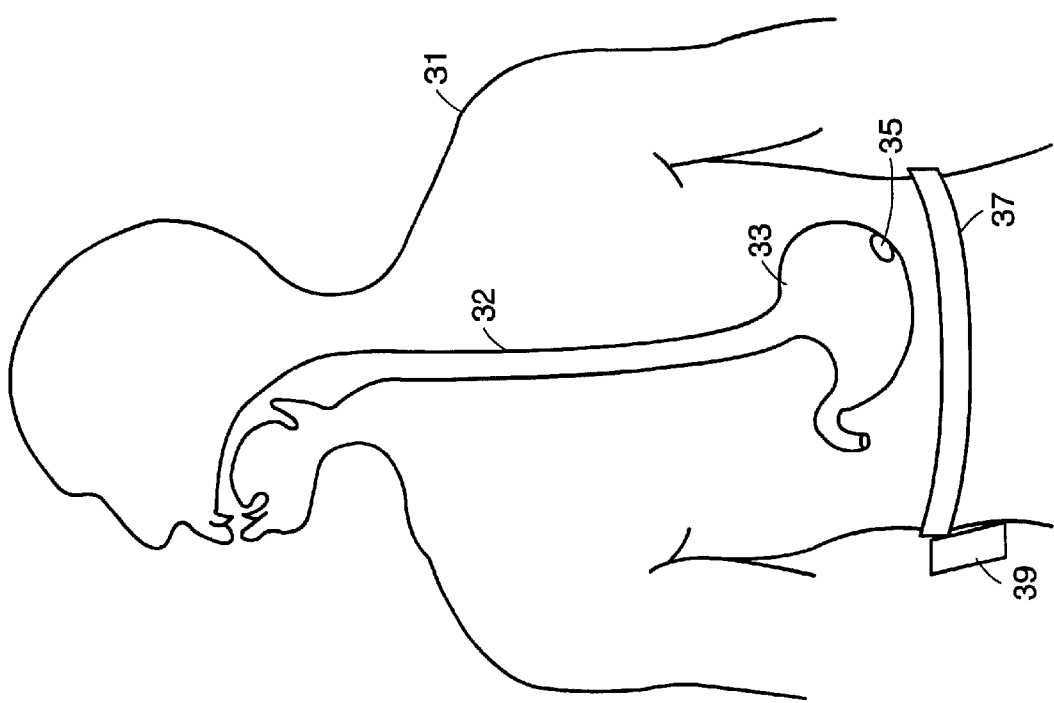
FIG. 3 illustrates a person wearing an antenna belt and a receiver mounted on the belt and a tissue spectroscopy capsule placed in the person's stomach after being swallowed.

FIG. 3 illustrates an operation of one embodiment of the invention. A patient 31 wears an antenna belt 37 and mounts a receiver 39 to the receiving antenna belt 37. The patient 31 swallows a tissue spectroscopy capsule 35, which may be sugar coated. The capsule 35 travels through the patient's esophagus 32 then to the stomach 33. While the capsule 35 travels toward the stomach 33, the light detectors and/or other sensors along with the transmitter in the capsule 35 collect and transmit information to the receiver 39. The receiver antenna belt 37 picks up signals from the transmitter. In one embodiment, spatial position and orientation of the capsule 35 is provided by a signal pattern of the antenna, which is oriented perpendicular to the central axis of the body.

Various parameters may be used to trigger signal transmission or recording so that energy in the capsule 35 is preserved for a period of time. The triggering event, for example, may be increased temperature, the presence of a specific fluorescence response, a pressure change or the like. A simple system may focus on just one parameter. In one embodiment, the tissue spectroscopy capsule 35 transmits signals to the receiver 39 only when the characteristic fluorescence response associated with cancer is detected.

When cancerous tissue is impinged with an excitation light, the cancerous tissue responds differently from normal tissue. By measuring the intensity and distribution of the emission peaks, one can distinguish cancerous tissue from normal tissue. Therefore, one or more light detectors with appropriate bandpass filtering may be used to detect tissue type and to generate a signal in response to that the tissue type.

For example, when both normal and cancerous tissues are excited by light having a wavelength of about 300 nanometers, the cancerous tissue fluoresces and emits a spectrum having a wavelength of about 360 nanometer, while the normal tissue fluoresces and emits a spectrum having a wavelength of about 400–440 nanometers. In addition, the peak amplitude of the cancerous tissue is greater than that of the normal tissue.

Figure 5A:
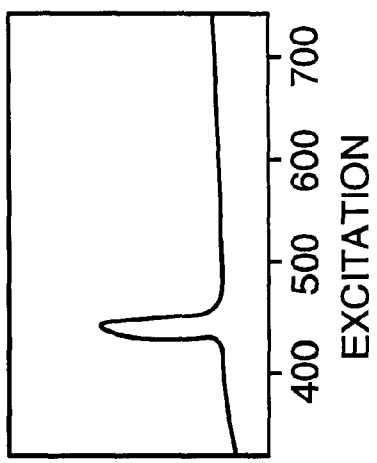
FIG. 5A is an example of an excitation spectrum used in tissue spectroscopy.
Figure 5B:
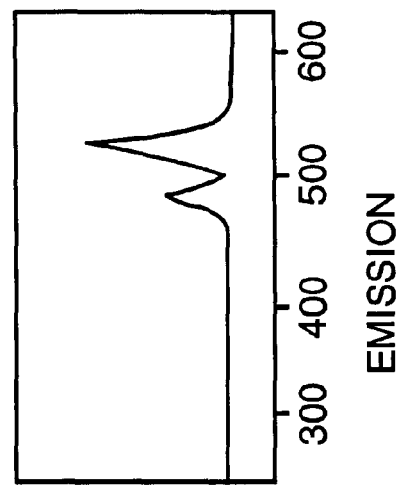
FIG. 5B is a characteristic emission spectrum of cancerous tissue illuminated by the excitation spectrum of FIG. 5A.

Another example of using excitation spectrum to identify cancerous tissue is shown in FIGS. 5A and 5B. FIG. 5A shows excitation wavelength at around 435 nm used to detect cancerous tissue in the esophagus, vagina, colon and bladder in addition to other places. FIG. 5B shows the resulting tissue autofluorescence that occurs when cancerous tissue is excited by the emission light of FIG. 5A. A strong peak at the 500 to 600 nanometer range is detected. In one embodiment, tissue is excited by light in the ultraviolet to blue range and spectroscopic properties of the illuminated tissue are detected.

In one embodiment, a timer inside the controller module 19 triggers light emission at pre-determined intervals and the receiver 39 simply records the number of times signal reflecting cancerous tissue is detected as the capsule 35 travels through the body. The intervals may be shorter initially as the capsule 35 moves quickly through the stomach and subsequently longer as the capsule 35 moves through the rest of the body. Such signals or "hits" may be recorded and later analyzed according to their duration, frequency and timing as compared with the relative position of the capsule 35 in the body to provide a first pass overview of the probability that cancerous conditions may exist in that patient 31. The presence of a large number of "hits" indicates the need for further examination.

After traveling through the gastrointestinal system, the capsule 35 can be normally expelled. In other systems of the body, the capsule 35 can behave more like an implant and can be retrieved with a snare, catheter or by surgery after use.

Referring to FIG. 4A, the transmitter system 41 disposed inside the capsule 13 of FIG. 2A includes light emitter 51, light detectors 49, a power source 43, a controller/timer module 45, an A-D converter, an oscillator 55 and a transmitter antenna 57. The power source 43 empowers the controller/timer module 45. In one embodiment, the power source 43 comprises a battery. The controller/timer 45 performs logical functions and housekeeping for the device and may be preprogrammed to operate at intervals or in response to signals, which may be converted to a digital format by the A-D converter 47. The output of the A-D converter 47 may be filtered and amplified (not shown) and sent via modulation line 53 to the oscillator 55. The oscillator 55 may be a simple surface acoustic wave oscillator or quartz crystal oscillator, which may have information superimposed upon it by modulation line 53. Subsequent modulated signals may be applied to the transmitter antenna 57 for transmission to a remote receiver shown in FIG. 4B.

Referring to FIG. 4B, the receiver system 61 collects radio frequency signals from the transmitter system 41 of FIG. 4A through a receiver antenna 63, which feeds the signals to a receiver module 65. The receiver module 65 includes an RF amplifier (not shown), which increases the signal level. The amplified signals are fed to a mixer and a heterodyne oscillator (also not shown) to an intermediate frequency amplifier, followed by detection and possibly further amplification stages. Such frequency conversion schemes are well known to those skilled in the radio art. The output from the receiver module 65 is fed via a signal line 67 to a data recorder 69. As previously described, the data thus delivered may be retransmitted to a further remote telephone line, cellular system or the like, or a low earth orbiting satellite system for delivery and reception by appropriate readers of such information, who may be trained to interpret the data and make medical diagnoses.

Figure 6:
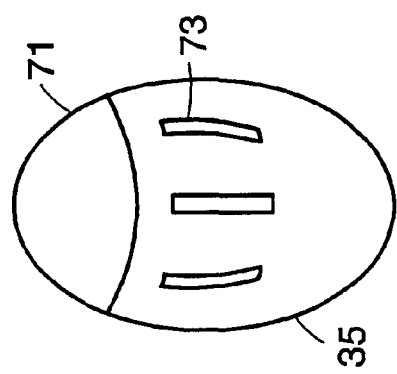
FIG. 6 is a perspective view of one embodiment of the tissue spectroscopy capsule.

Referring to FIG. 6, the tissue spectroscopy capsule 35 is elliptical or egg shaped and includes an optically transparent window 71 on an outer surface of the capsule 35. The position of the window is important as it determines which tissue is being diagnosed. As the capsule 35 travels through the body, the capsule 35 orients itself so that the major axis is generally aligned with the plane or surface to which the capsule 35 is in contact. For example, FIG. 3 shows the capsule 35 having its broad side in contact with the mucosal lining of the stomach 33. Anticipating this natural orientation of an egg shaped object, the window 71 may be positioned so that internal sensing components such as light detectors, electrodes or chemical sensors located near the inner surface of the egg shaped capsule 35 are in good contact with the tissue walls. Orthogonal orientation may be provided by situating the sensors around the middle periphery of an egg shaped capsule 35. In the embodiment of FIG. 6, electrodes 73 are placed on the outer surface of the capsule 35 to confirm that the capsule 35 is oriented in a certain way, thereby enhancing the reliability and predictability of the data collected. Electrodes 73 placed on predetermined locations on the capsule 35 can provide orientation information by measuring resistance, which is lower when the electrodes 73 are contacting the tissue walls.

In one embodiment, the window 71 is located on a pre-selected area of the capsule 35. In another embodiment, the entire capsule 35 is essentially transparent and the sensors within the capsule 35 aim specific locations inside the body. In still another embodiment, the tissue spectroscopy capsule is sphere shaped. Random orientation is provided by utilizing the sphere shaped capsule.

In one embodiment, a tissue spectroscopy apparatus of the invention, whether it is a probe or a capsule, is sealed so that fluids or contaminants may not flow in or out. In another embodiment, the apparatus permits delivery of fluid to a tissue region being diagnosed. In addition, although the invention is particularly useful for diagnosing internal tissue, the invention as described may be useful for applications outside the body, where a miniaturized, disposable and relatively inert test of otherwise inaccessible regions may be desired.

The portable tissue spectroscopy instruments of the present invention are simple and inexpensive devices, which can be used to access areas within the body to transmit useful information about the state of tissue in its proximity. The devices are user-friendly, as they either permit the devices to be held by hand, or be swallowed by a person or be implanted in a person providing maximum comfort to the person. The devices are also self-contained and portable, thereby eliminating the need for the use of bulky and painful endoscopes. In addition, economical mass production of the devices can be achieved with ordinary silicon based integrated circuit design to make the emitters and the sensors, in addition to assembling the power source within the device housing.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A tissue spectroscopy apparatus, comprising:
 a housing insertable in a cavity of a body;
 at least one light source disposed in the housing for illuminating tissue in the body, the light source emitting an output light;
 at least one light detector disposed in the housing for detecting spectroscopic properties of the illuminated tissue;
 a filter on each said at least one light detector, the filter admitting light within a predetermined wavelength range corresponding to a physiological characteristic of interest;
 a power source disposed in the housing for powering said at least one light source and said at least one light detector; and
 at least one indicator located on a proximal end of the housing for displaying an indication of the spectroscopic properties of the illuminated tissue.

2. The tissue spectroscopy apparatus of claim 1 further comprising a control module disposed in the housing in communication with the power source.

3. The tissue spectroscopy apparatus of claim 1 wherein the at least one light source comprises a light emitting diode.

4. The tissue spectroscopy apparatus of claim 3 wherein the light emitting diode is a blue light emitting diode.

5. The tissue spectroscopy apparatus of claim 1 wherein the at least one light source comprises a laser.

6. The tissue spectroscopy apparatus of claim 1 wherein the housing comprises a window disposed adjacent the at least one light source.

7. The tissue spectroscopy apparatus of claim 6 wherein a distal end of the housing is angled to provide better contact between the window and the tissue.

8. The tissue spectroscopy apparatus of claim 6 wherein the window comprises a diffuser for uniformly illuminating the tissue.

9. The tissue spectroscopy apparatus of claim 1 wherein the power source comprises a battery.

10. The tissue spectroscopy apparatus of claim 1 wherein the housing is a probe having a distal end insertable in the cavity and a hand-holdable proximal end remaining outside the body.

11. The tissue spectroscopy apparatus of claim 10 further comprising an actuator disposed adjacent the proximal end of the housing for actuating the apparatus.

12. The tissue spectroscopy apparatus of claim 10 wherein the probe comprises a flexible cover material.

13. The tissue spectroscopy apparatus of claim 1, wherein the at least one light detector comprises first and second light detectors, the first detector having a first filter admitting light within a first predetermined wavelength range and the second detector having a second filter admitting light within a second predetermined wavelength range differing from the first predetermined wavelength range.

14. The tissue spectroscopy apparatus of claim 13, wherein the at least one indicators comprises a first indicator electrically connected to the first detector, and a second indicator electrically connected to the second detector.

15. The tissue spectroscopy apparatus of claim 13, wherein the first wavelength range comprises a first wavelength of light from a cancerous tissue type when said cancerous tissue is illuminated by the at least one light source, and wherein the second wavelength range comprises a second wavelength of light from a non-cancerous tissue type when said non-cancerous tissue is illuminated by the at least one light source.

16. The tissue spectroscopy apparatus of claim 1 wherein the filter comprises a bandpass filter.

17. The tissue spectroscopy apparatus of claim 1 wherein the filter comprises a portion of the housing.

18. The tissue spectroscopy apparatus of claim 1 wherein the at least one detector is adjacent the at least one light source such that the at least one detector receives light from the at least one light source before said light interacts with the tissue.

19. The tissue spectroscopy apparatus of claim 1 wherein the predetermined wavelength range comprises a wavelength of light from a target tissue type after said target tissue type is illuminated by the at least one light source.

20. The tissue spectroscopy apparatus of claim 1 wherein the target tissue type comprises a cancerous tissue.

21. The tissue spectroscopy apparatus of claim 1 wherein the predetermined wavelength range received by the at least one detector comprises a range between about 300 nm and about 600 nm.

22. The tissue spectroscopy apparatus of claim 1, wherein the at least one light source illuminates at least at a wavelength of about 300 nm, and the predetermined wavelength range received by the at least one detector comprises a wavelength of about 360 nm.

23. The tissue spectroscopy apparatus of claim 1 wherein the at least one light source illuminates at least at a wavelength of about 435 nm, and the predetermined wavelength range received by the at least one detector comprises a range between about 500 nm and about 600 nm.

24. The tissue spectroscopy apparatus of claim 1 wherein the predetermined wavelength range is adjustable.

25. The tissue spectroscopy apparatus of claim 24 wherein the filter comprises a portion of the housing.

26. The tissue spectroscopy apparatus of claim 1 wherein the predetermined wavelength range is adjusted through adjusting the thickness of the filter.

27. The tissue spectroscopy apparatus of claim 1 wherein the filter contains a dye, and wherein the predetermined wavelength range is adjusted through adjusting the concentration of the dye.

28. The tissue spectroscopy apparatus of claim 1, further comprising an output filter disposed in a pathway of the output light, said output filter filters the output light such that the output light in an output wavelength range reaches the tissue.

29. The tissue spectroscopy apparatus of claim 28 wherein the output wavelength range comprises the range of ultraviolet light.

30. The tissue spectroscopy apparatus of claim 29 wherein the output wavelength range is adjustable.

31. The tissue spectroscopy apparatus of claim 28 wherein the output filter comprises an interference filter.

32. The tissue spectroscopy apparatus of claim 1, further comprising a frequency multiplier disposed in a pathway of the output light, said frequency multiplier amplifies the frequency of the output light.

33. The tissue spectroscopy apparatus of claim 32, wherein the frequency multiplier comprises an optically non-linear substance.

34. The tissue spectroscopy apparatus of claim 32, further comprising a wave matching layer.

35. The tissue spectroscopy apparatus of claim 1, further comprising a lens disposed in a pathway of the output light.

36. A method for performing a tissue spectroscopy, comprising:
  (a) inserting a probe in a body cavity, such that a distal end of the probe is positioned adjacent a tissue, while a proximal end remains outside the body cavity;
  (b) illuminating the tissue in the body with an output light emitted by at least one light source disposed in the probe;
  (c) using a filter to admit input light from the illuminated tissue only within a wavelength range corresponding to a physiological characteristic of interest;
  (d) detecting properties of the filtered input light with at least one light detector disposed in the probe; and
  (e) displaying the detected properties on at least one indicator located on the proximal end of the probe, the properties indicating characteristics of the illuminated tissue.

37. The method of claim 36 wherein step (b) comprises illuminating the tissue with light in an ultraviolet to blue range.

38. The method of claim 36 wherein step (c) comprises admitting light in the range from about 300 nm to 500 nm.

39. The method of claim 36, wherein the filter is a bandpass filter.

40. The method of claim 36, wherein step (c) is accomplished using a portion of the probe.

41. The method of claim 36, wherein step (c) further comprises the step of adjusting the wavelength range.

42. The method of claim 41, wherein the step of adjusting the wavelength range comprises adjusting the thickness of the filter.

43. The method of claim 42, wherein the filter comprises a portion of the probe, the step of adjusting the thickness of the filter comprising repositioning the at least one detector in the probe.

44. The method of claim 41, wherein the filter contains a dye, step (c) further comprising adjusting the concentration of the dye.

45. The method of claim 44, wherein the filter comprising a portion of the probe, adjusting the concentration of the dye of the filter comprising repositioning the at least one detector in the probe.

46. The method of claim 44, wherein step (c) comprises using at least a first filter and a second filter, the first filter admitting input light expected from a cancerous tissue, the second filter admitting input light expected from a non-cancerous tissue.

47. The method of claim 46, wherein step (d) comprises using a first detector to detect light filtered by the first filter, and using a second detector to detect light filtered by the second filter.

48. The method of claim 47, wherein step (e) comprises electrically connecting a first indicator to the first detector, and electrically connecting a second indicator to the second detector.

49. The method of claim 36, wherein step (c) comprises admitting input light expected from a cancerous tissue.

50. The method of claim 36, further comprising filtering the output light before the output light reaches the tissue.

51. The method of claim 36, further comprising amplifying the output light before the output light reaches the tissue.

52. The method of claim 36, further comprising focusing the output light before the output light reaches the tissue.

53. A tissue spectroscopy apparatus, comprising:
   a housing insertable in a cavity of a body;
   at least one light source disposed in the housing for illuminating tissue in the body, the light source emitting an output light;
   a plurality of light detectors disposed in the housing for detecting spectroscopic properties of the illuminated tissue;
   a filter on at least one of the light detectors, the filter admitting light within a predetermined wavelength range corresponding to a physiological characteristic of interest;
   a power source disposed in the housing for powering at least one of the light sources and at least one of the light detectors; and
   an indicator located on a proximal end of the housing for displaying an indication of the spectroscopic properties of the illuminated tissue.

54. The tissue spectroscopy apparatus of claim 53, wherein the apparatus comprises first and second light detectors, the first detector having a first filter admitting light within a first predetermined wavelength range and the second detector having a second filter admitting light within a second predetermined wavelength range different from the first predetermined wavelength range.

55. The tissue spectroscopy apparatus of claim 53, wherein at least one of the plurality of detectors is adjacent the at least one light source such that the at least one of the plurality of detectors receives light from the at least one light source before said light interacts with the tissue.

* * * * *